United States Patent
Suzuki et al.

(10) Patent No.: US 11,096,561 B2
(45) Date of Patent: Aug. 24, 2021

(54) CONTROL APPARATUS FOR INSERTION DEVICE AND INSERTION DEVICE

(71) Applicant: OLYMPUS CORPORATION, Tokyo (JP)

(72) Inventors: Takashi Suzuki, Hino (JP); Fumiyuki Onoda, Tama (JP); Keijiro Omoto, Hachioji (JP); Takashi Yamashita, Hachioji (JP); Yasuaki Natori, Akishima (JP); Yoshitaka Umemoto, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 395 days.

(21) Appl. No.: 15/966,102

(22) Filed: Apr. 30, 2018

(65) Prior Publication Data

US 2018/0242819 A1 Aug. 30, 2018

Related U.S. Application Data

(63) Continuation of application No. PCT/JP2017/015928, filed on Apr. 20, 2017.

(30) Foreign Application Priority Data

May 24, 2016 (JP) .............................. JP2016-103454

(51) Int. Cl.
*A61B 1/00* (2006.01)
*G02B 23/24* (2006.01)

(52) U.S. Cl.
CPC .............. *A61B 1/0016* (2013.01); *A61B 1/00* (2013.01); *A61B 1/00006* (2013.01);
(Continued)

(58) Field of Classification Search
CPC .............. A61B 1/00156; A61B 1/0016; G02B 23/2484
See application file for complete search history.

(56) References Cited

U.S. PATENT DOCUMENTS

| | | | | |
|---|---|---|---|---|
| 2008/0009675 A1* | 1/2008 | Kura | ................... | A61B 1/00156 600/137 |
| 2008/0086029 A1* | 4/2008 | Uchiyama | .......... | A61B 1/00039 600/114 |

FOREIGN PATENT DOCUMENTS

| | | |
|---|---|---|
| JP | 2008-093029 A | 4/2008 |
| JP | 2014-068895 A | 4/2014 |

(Continued)

OTHER PUBLICATIONS

English translation of International Preliminary Report on Patentability dated Dec. 6, 2018 together with the Written Opinion received in related International Application No. PCT/JP2017/015928.

(Continued)

*Primary Examiner* — Alexandra L Newton
*Assistant Examiner* — Rynae Boler
(74) *Attorney, Agent, or Firm* — Scully, Scott, Murphy & Presser, P.C.

(57) ABSTRACT

A control apparatus includes a drive current detector detecting a drive current value driving the motor to drive a rotation body, and a controller controlling the motor in a speed control method which controls the motor so that a rotation speed of the motor reaches a targeted rotation speed until the drive current value reaches a predetermined switching value, and, when the drive current value reaches the switching value, controlling the motor by switching to a torque control method which controls the motor so that the drive current value reaches a targeted current value.

5 Claims, 4 Drawing Sheets

(52) U.S. Cl.
CPC ......... *G02B 23/24* (2013.01); *G02B 23/2484* (2013.01); *A61B 1/00009* (2013.01)

(56) References Cited

FOREIGN PATENT DOCUMENTS

| | | |
|---|---|---|
| WO | WO 2014/003064 A1 | 1/2014 |
| WO | WO 2015/118773 A1 | 8/2015 |

OTHER PUBLICATIONS

International Search Report dated Jul. 4, 2017 issued in PCT/JP2017/015928.
Chinese Office Action dated Aug. 5, 2019 received in 201780003773.7.

\* cited by examiner

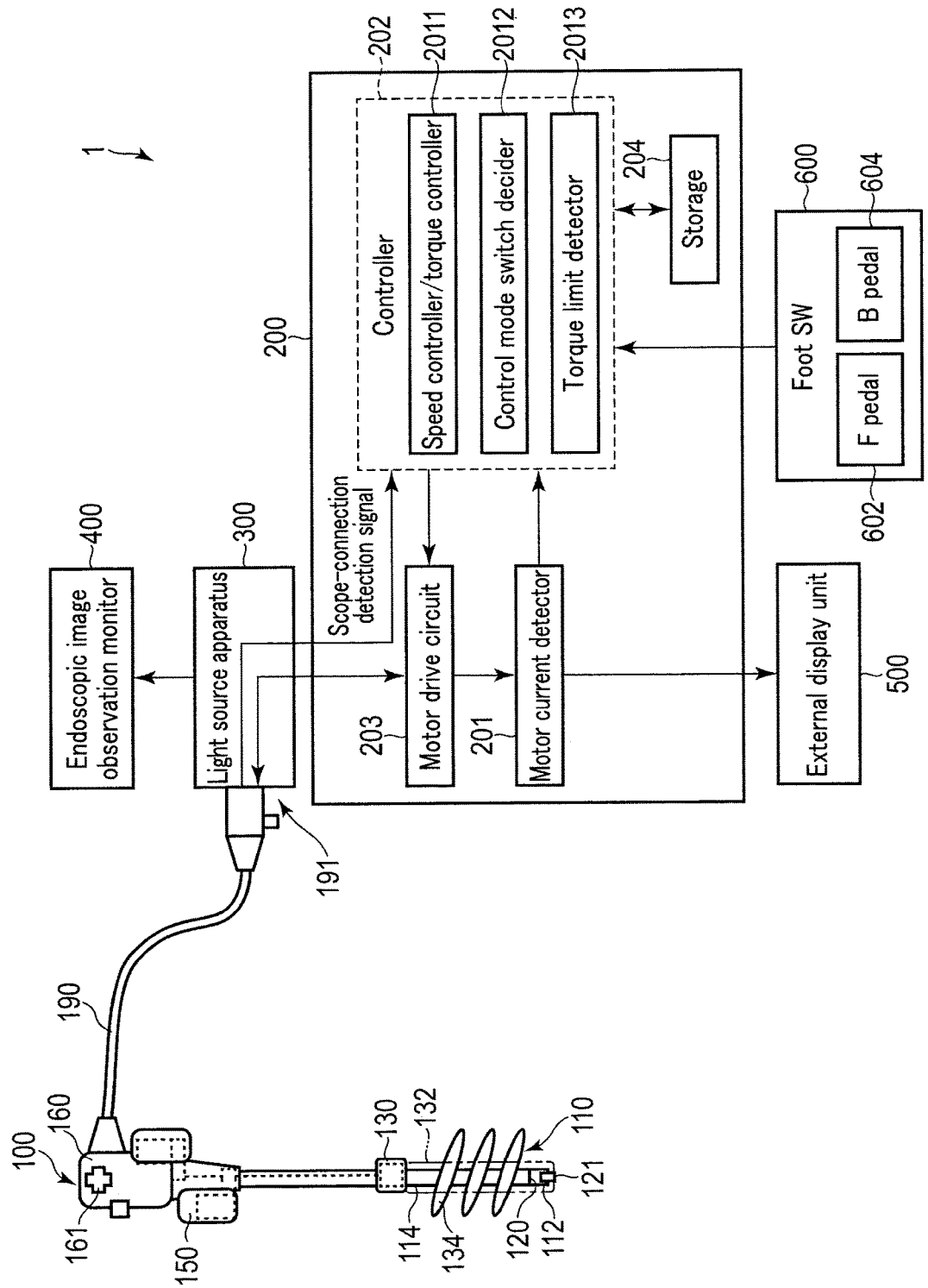
F I G. 1

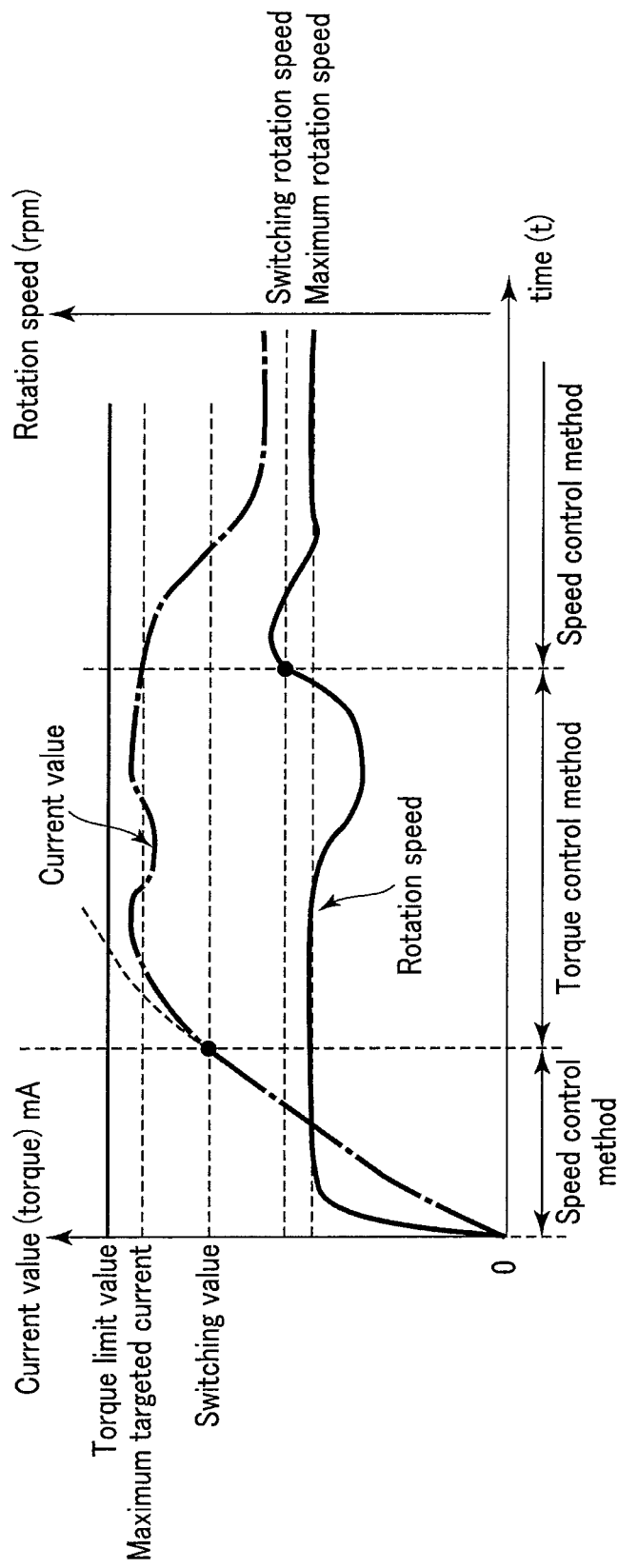
F I G. 3

CONTROL APPARATUS FOR INSERTION DEVICE AND INSERTION DEVICE

CROSS-REFERENCE TO RELATED APPLICATIONS

This application is a Continuation Application of PCT Application No. PCT/JP2017/015928, filed Apr. 20, 2017 and based upon and claiming the benefit of priority from the prior Japanese Patent Application No. 2016-103454, filed May 24, 2016, the entire contents of both of which are incorporated herein by reference.

BACKGROUND OF THE INVENTION

1. Field of the Invention

The present invention relates to a control apparatus for an insertion device and to an insertion device.

2. Description of the Related Art

Insertion devices such as endoscopic devices are commonly inserted endolumenally. One of these insertion devices is known as a self-propelled insertion device. Such a self-propelled insertion device causes the insertion section to, for example, retreat by way of thrust from the motor rotating the rotation body provided in the circumference of the insertion section. Such an insertion device assists the inserting or removing operations by the user.

Common insertion devices have a torque limit function which causes the rotation of the motor to stop when the motor torque (motor current) reaches or exceeds a predetermined value. As an example, Jpn. Pat. Appln. KOKAI Publication No. 2008-093029 suggests a rotating self-propelled endoscope system, configured to change, according to how much the insertion section is inserted, a predetermined torque limit value used for deciding whether or not to actuate the torque limit function.

BRIEF SUMMARY OF THE INVENTION

A control apparatus according to a first aspect of the invention is a control apparatus is a control for an insertion device comprising a long and thin insertion section, a rotate-driven self-propelling mechanism causing the insertion section to retreat, and a motor feeding driving force to the self-propelling mechanism. The control apparatus comprises: a drive current detector detecting a drive current value driving the motor; and a controller controlling the motor in a speed control method which controls the motor so that a rotation speed of the motor reaches a targeted rotation speed until the drive current value reaches a predetermined switching value, and, when the drive current value reaches the switching value, controlling the motor by switching to a torque control method which controls the motor so that the drive current value reaches a targeted current value.

An insertion device according to a second aspect of the invention comprises: a long and thin insertion section; a rotate-driven self-propelling mechanism causing the insertion section to retreat; a motor feeding driving force to the self-propelling mechanism; a drive current detector detecting a drive current value for driving the motor; and a controller controlling the motor in a speed control method which controls the motor so that a rotation speed of the motor reaches a targeted rotation speed until the drive current value reaches a predetermined switching value, and, when the drive current value reaches the switching value, controlling the motor by switching to a torque control method which controls the motor so that the drive current value reaches a targeted current value.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute apart of the specification, illustrate embodiments of the invention, and together with the general description given above and the detailed description of the embodiments given below, serve to explain the principles of the invention.

FIG. 1 is a schematic view showing the configuration of an endoscope system serving as an example of an insertion device according to an embodiment of the present invention.

FIG. 3 is a view showing the changes the motor control method during the process shown in FIG. 2.

DETAILED DESCRIPTION OF THE INVENTION

Figure 2:
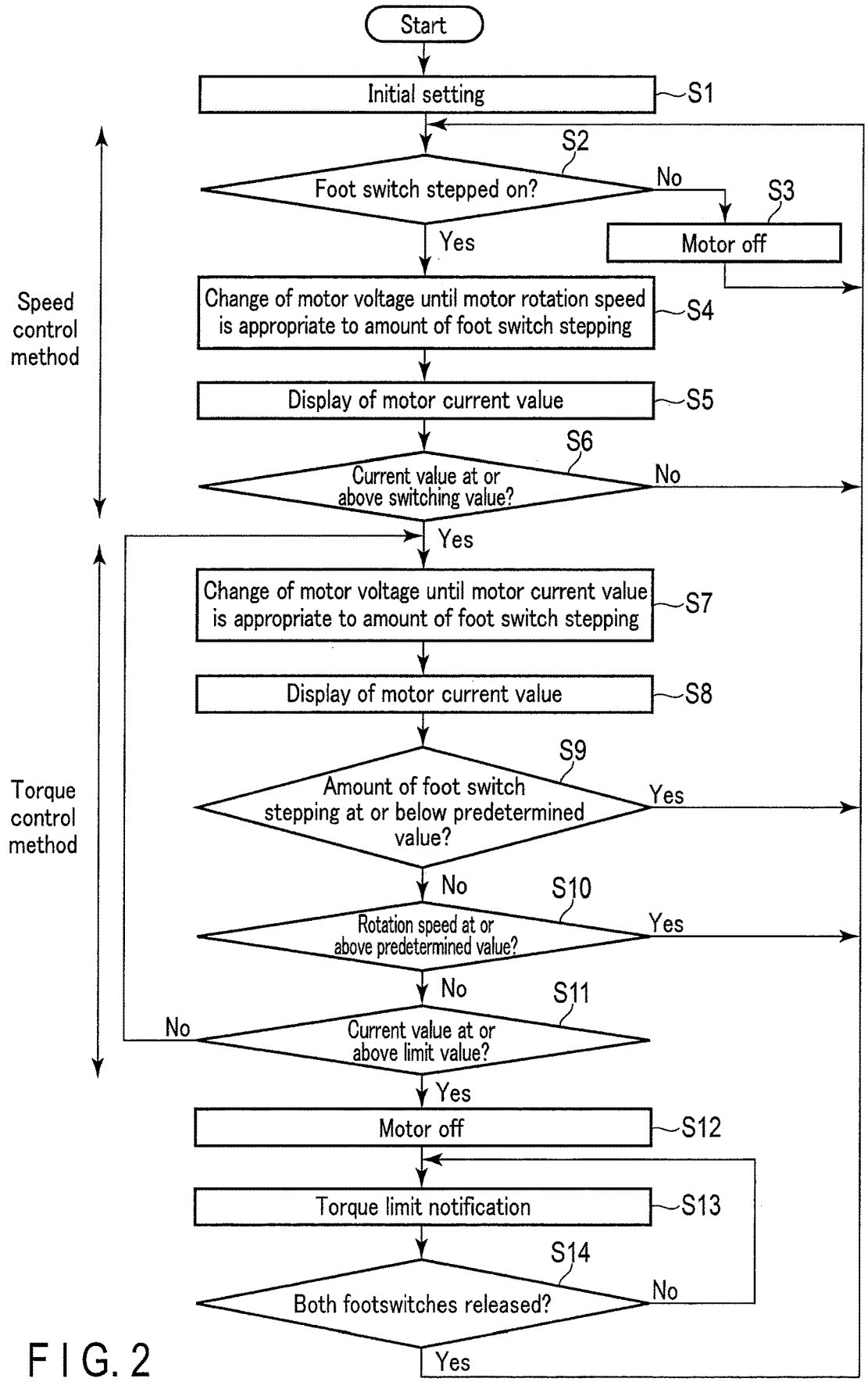
FIG. 2 is a flowchart providing an example of the performances of the endoscope system.

The embodiments of the present invention will hereinafter be described with reference to the drawings. FIG. 1 is a schematic view showing the configuration of an endoscope system serving as an example of an insertion device according to an embodiment of the present invention. As shown in the drawing, the endoscope system 1 comprises an endoscope 100, a control apparatus 200, a light source apparatus 300, an endoscopic image observation monitor 400, an external display unit 500 and a foot switch 600. The endoscope 100 is a rotary self-propelled endoscope, having an insertion section 110. The insertion section 110 is long and thin, and is configured to be inserted into the live body. The endoscope 100 further comprises a control unit 160 for performing the various operations of the endoscope 100. The control unit 160 is held by the user. The side where the distal end of the insertion section 110 is located shall be referred to as the "distal-end side", and the side where the control unit 160 of the insertion section 110 is located shall be referred to as the "proximal-end side". The direction along the distal-end side to the proximal-end side of the insertion section 110 shall be referred to as the "longitudinal direction". The control unit 160 and the light source apparatus 300 of the endoscope 100 are connected via a universal cable 190.

The insertion section 110 comprises a hard section 112 at the distal end and a bending section 114. The hard section 112 at the distal end is the most distal part of the insertion section 110, and it is configured not to bend. The bending section 114 is the part formed on the proximal-end side of the hard section 112 at the distal end, and it comprises a part which actively bends appropriate to the operations of the operating unit 161 that is provided at the control unit 160, and a part which passively bends appropriate to the external force being applied.

The hard section 112 at the distal end comprises an imaging element 120 and an illumination lens 121. The imaging element 120 generates image signals based on, for example, a subject image taken at the distal-end side of the insertion section 110. The image signals generated by the imaging element 120 are then transmitted to the light source apparatus 300 via a signal line for image signals which extends through the insertion section 110 and the universal cable 190 but which is not shown in the drawings. The illumination lens 121 diffuses and emits light being led from the light source apparatus 300 via optical fiber that extends through the insertion section 110 and the universal cable 190 but which is not shown in the drawings.

The bending section 114 of the insertion section 110 is mounted thereunto a rotation section 130 for transferring the driving force of the motor 150 that is built into the control unit 160. The distal-end side of the rotation section 130 is mounted thereunto a power spiral tube 132 that is the rotation body. The power spiral tube 132 is tubular and made of an elastic material such as, for example, rubber or resin, and is mounted rotatably about the longitudinal axis of the bending section 114. The outer periphery of the power spiral tube 132 is provided with a spiral-shaped fin 134 provided along the longitudinal axis of the power spiral tube 132. The power spiral tube 132 may, however, also be configured to be removable from the rotation section 130.

The power spiral tube 132 is connected to the motor 150 which is an actuator provided at the control unit 160. The motor 150 is connected to the light source apparatus 300 via a signal line for actuator current signals which extends through the control unit 160 and the universal cable 190 but which is not shown in the drawings. The motor 150 is connected to the control apparatus 200 via the light source apparatus 300.

The motor 150 is operated by operations using the foot switch 600. The torque of the motor 150 is transferred to the rotation section 130. Consequently, the fin 134 provided at the power spiral tube 132 rotates about the longitudinal axis.

When the fin 134 rotates while, for example, the wall part such as an inner wall of a lumen is contacted, a frictional force is generated. When, for example in the small intestine or the large intestine, the fin 134 contacts a pleat in the inner wall of the small intestine or the large intestine, a frictional force is exerted unto the insertion section 110. The insertion section 110 can propel itself because of this frictional force. The insertion section 110 which propels itself assists the user's inserting or removing operations of the insertion section 110. The motor 150 further comprises a pulse generator. This pulse generator generates pulse signals (rotation speed signals) in accordance with the rotation speed of the motor 150, and inputs these rotation speed signals via a rotation speed signal line into the light source apparatus 300. The light source apparatus 300 then inputs the rotation speed signals into the control apparatus 200. The rotation speed of the motor 150 is controlled by these rotation speed signals.

The endoscopic image observation monitor 400 comprises, for example, a common display device such as a liquid crystal display. The endoscopic image observation monitor 400 displays endoscopic images based on, for example, the image signals obtained by the imaging element 120.

The foot switch 600 comprises a forward pedal (F pedal) 602 and a backward pedal (B pedal) 604. The foot switch 600 is an operating unit for designating a targeted rotation speed and a targeted current value. When the user steps on the F pedal 602, the pedal issues a designation signal causing the motor 150 to rotate clockwise, and when the user steps on the B pedal 604, the pedal issues a designation signal causing the motor 150 to rotate counter-clockwise. Besides, the F pedal 602 and the B pedal 604 are configured to issue signals which have sizes that are appropriate to the amounts with which the pedals are being stepped upon.

The external display unit 500 is a display device using display elements such as LEDs to display for indicating to the user, based on the motor current value input from a motor current detector 201, the size of the torque (motor current) of the motor 150.

The control apparatus 200 controls each element of the endoscope system 1, and comprises the motor current detector 201, a controller 202 and a motor drive circuit 203.

The motor current detector 201 being a drive current detector detects the motor current value that is the drive current output from the motor drive circuit 203, and inputs the detected motor current value to the external display unit 500.

The controller 202 is constituted of, for example, a CPU or an ASIC, and comprises the functions of a speed controller/torque controller 2011, a control method switch decider 2012, and a torque limit detector 2013. Each of these functions of the controller 202 may be realized by a single hardware or software unit, or by a plurality of hardware or software units. Part of the functions may also be provided elsewhere than at the controller 202.

The speed controller/torque controller 2011 controls the motor 150 either when using the speed control method or the torque control method. When using the speed control method, the motor 150 is controlled to make the rotation speed reach the targeted rotation speed. By using the torque control method, the motor 150 is controlled to cause the motor current value (corresponds to the torque value of the motor 150) to reach a targeted current value. By controlling the motor 150 using the speed control method, the speed controller/torque controller 2011 inputs a targeted rotation speed value to the motor drive circuit 203. The targeted rotation speed value is set, for example, appropriate to the amount at which the foot switch 600 is being stepped on. By controlling the motor 150 using the torque control method, the speed controller/torque controller 2011 inputs the targeted current value to the motor drive circuit 203. The targeted current value is greater than the switching value described further below in detail, but smaller than the torque limit value, and set, for example, appropriate to the amount at which the foot switch 600 is being stepped on.

The control method switch decider 2012 decides whether or not the motor control method be switched at the speed controller/torque controller 2011. Specifically, while the motor current value does not reach the switching value, the control method switch decider 2012 decides that the motor control method be switched to the speed control method using the speed controller/torque controller 2011, and when the motor current value reaches or exceeds the switching value, the control method switch decider 2012 decides that the motor control method be switched to the torque control method using the speed controller/torque controller 2011. After the control method switch decider 2012 switched the motor control method to the torque control method, and when the amount at which the foot switch 600 is stepped on reaches or fallen below a predetermined value or when the rotation speed of the motor 150 reaches or exceeds a predetermined value, the control method switch decider 2012 decides that the motor control method be switched to the speed control method. The switching will be described further below in greater detail.

The torque limit detector 2013 determines whether or not the motor current value detected by the motor current detector 201 is at or above the torque limit value being a predetermined current threshold. If the torque limit detector 2013 determines that the motor current is at or above the torque limit value, the torque limit detector 2013 decides that the torque limit be imposed onto the motor 150. "Torque limit" in this context means a process of controlling the rise in torque of the motor 150 by stopping the motor 150 through stopping the supply of motor current from the motor drive circuit 203 to the motor 150.

By using the speed control method, the motor drive circuit 203 retrieves, per a predetermined sampling time, a rotation speed signal input from the pulse generator of the control unit 160, converts the retrieved rotation speed signal into a feedback signal, and changes the motor voltage so that the rotation speed of the motor 150 reaches a targeted rotation speed appropriate to the amount at which the foot switch 600 is being stepped on. Similarly, by using the torque control method, the motor drive circuit 203 changes the motor voltage so that the motor current reaches a targeted current value appropriate to the amount at which the foot switch 600 is being stepped on.

The storage unit 204 is a storage medium to which content is stored even when the power is cut off, such as a FLASH memory; it stores both a program for operating the control apparatus 200 and data such as the switching value and the torque limit value.

The light source apparatus 300 comprises a scope-connection detection connector 191. Via the scope-connection detection connector 191, the endoscope 100 is mounted unto the light source apparatus 300. When the endoscope 100 is mounted unto the light source apparatus 300 via the scope-connection detection connector 191, the endoscope 100 inputs a scope-connection detection signal to the controller 202 of the control apparatus 200. In this way, the controller 202 detects that the endoscope 100 is mounted. The light source apparatus 300 further comprises, for example, white-light LEDs or xenon lamps, and it inputs light to an optical fiber inside the universal cable 190 not shown in the drawings. The light is then emitted from the illumination lens 121. The light source apparatus 300 performs an image process unto the image signals input via the insertion section 110 and the universal cable 190. The light source apparatus 300 then inputs the processed image signals to the endoscopic image observation monitor 400 to display the endoscopic image at the endoscopic image observation monitor 400.

Hereinafter, operations of the endoscope system 1 according to an embodiment of the present invention shall be described. FIG. 2 is a flowchart showing an example of the operations of the endoscope system 1. The operations shown in FIG. 2 are controlled by the controller 202 included in the control apparatus 200. The operations begin when, for example, the power of the endoscope system 1 is switched on. Concurrent with the operations shown in FIG. 2, the process of displaying endoscopic images at the endoscopic image observation monitor 400 is performed based on the image signals obtained by the imaging element 120. FIG. 3 is a view showing the changes of the motor control method during the process shown in FIG. 2.

In step S1, the controller 202 conducts an initial setting. In the initial setting, the controller 202, for example, checks the connections of the endoscope 100 and initializes the various setting values. After the initial setting, the process continues to step S2. From here on, the present description continues under the assumption that the endoscope 100 is ready-mounted, but the process in fact does not continue to step S2 until the endoscope 100 is ready-mounted.

In step S2, the controller 202 determines whether or not the foot switch 600 is stepped on. "Stepped on" in this context relates either to the F pedal 602 or the B pedal 604. If it is determined in step S2 that the foot switch 600 is not stepped on, the process continues to step S3. If it is determined in step S2 that the foot switch 600 is stepped on, the process continues to step S4.

In step S3, the controller 202 stops the motor 150 by stopping the supply of motor current from the motor drive circuit 203. Then, the process returns to step S2.

Figure 4A:
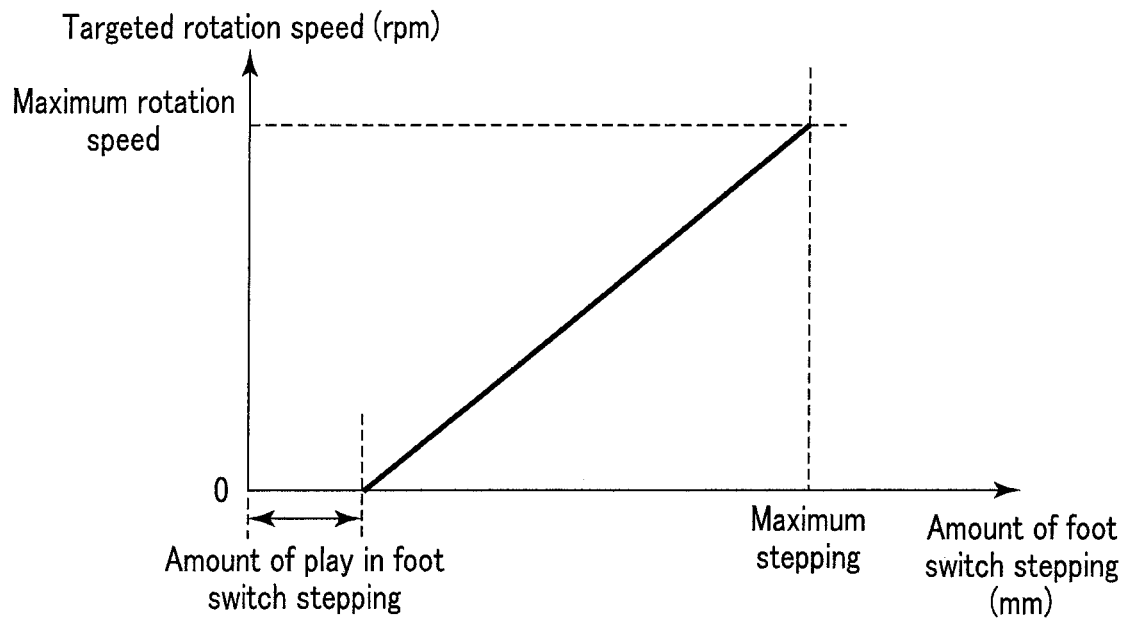
FIG. 4A is a view showing the relationship between the amount that the foot switch is being stepped on and the targeted rotation speed when using the speed control method.

In step S4, the controller 202 controls the motor 150 by using the speed control method. In other words, the controller 202 changes the motor voltage so that the rotation speed of the motor 150 reaches the targeted rotation speed that is appropriate to the amount at which the foot switch 600 is stepped on. Then, the process continues to step S5. FIG. 4A is a view showing the relationship between the amount at which the foot switch 600 is stepped on and the targeted rotation speed when using the speed control method. As shown in FIG. 4A, the targeted rotation speed when using the speed control method changes linearly in relation to the amount at which the foot switch 600 is stepped on. When the amount at which the foot switch 600 is stepped on reaches the maximum stepping amount, the targeted rotation speed reaches the maximum rotation speed. Thus, as long as the control method of the motor 150 is the speed control method, a rotation speed is maintained which, as shown in FIG. 3, is appropriate to the amount at which the foot switch 600 is stepped on. After the rotation speed of the motor 150 reaches the maximum rotation speed, the rotation speed of the motor 150 is kept at this maximum rotation speed. To then maintain the rotation speed appropriate to the amount at which the foot switch 600 is stepped on, the motor 150 must be driven against the load from the body. For this purpose, it is therefore necessary to increase the motor voltage. Consequently, by using the speed control method, the torque (motor current) of the motor 150 rises appropriate to the amount that the foot switch 600 is stepped on.

In the example shown in FIG. 4A, the targeted rotation speed is configured not to increase above 0 until the amount at which the foot step is stepped on exceeds a predetermined amount of play in stepping on the foot switch. The reason behind this is to correctly detect the user's intention of stepping on the foot switch 600. By setting such amount of play in stepping on the foot switch, false operation of the insertion section 110 due to non-intentional stepping on the foot switch 600 by the user can be prevented.

In step S5, the controller 202 displays the motor current value (torque value) detected by the motor current detector 201 on the external display unit 500. The torque value is displayed by, for example, lighting the number of gauges appropriate to the motor current value.

In step S6, the controller 202 determines whether or not the motor current value detected by the motor current detector 201 is at or above a set switching value. The switching value is a predetermined current value smaller than the torque limit value, and stored to the storage unit 204. If it is determined in step S6 that the motor current value detected by the motor current detector 201 is below the set switching value, the process returns to step S2. In that case, the control of the motor 150 is continued when using the speed control method. If it is determined in step S6 that the motor current value detected by the motor current detector 201 is at or above the set switching value, the process returns to step S7.

Figure 4B:
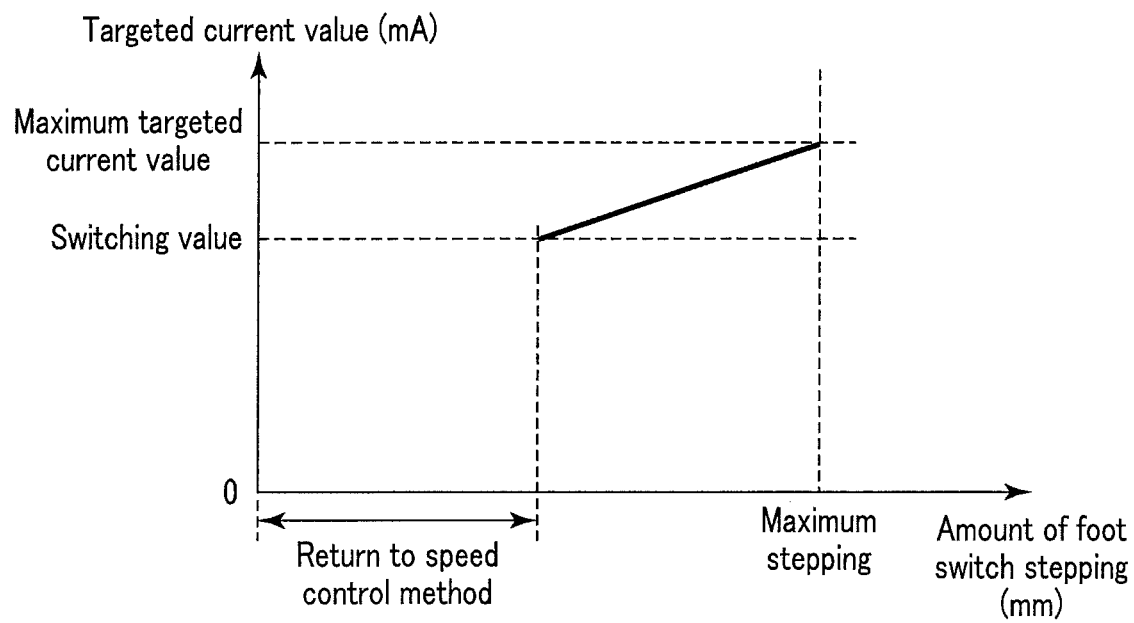
FIG. 4B is a view showing the relationship between the amount that the foot switch is being stepped on and the targeted current value when using the torque control method.

In step S7, the controller 202 controls the motor 150 by using the torque control method. In other words, the controller 202 changes the motor voltage so that the motor current value reaches a targeted current value that is appropriate to the amount at which the foot switch 600 is stepped on. The process then continues to step S8. The targeted current value is decided according to the amount at which the foot switch 600 is stepped on; it is a current value greater than the switching value but smaller than the torque limit value. FIG. 4B is a view showing the relationship between the amount at which the foot switch 600 is stepped on and the targeted rotation speed when using the torque control method. As shown in FIG. 4B, the targeted current value is configured to linearly change in relation to the amount at which the foot switch 600 is stepped on when using the torque control method. When the amount at which the foot switch 600 is stepped on reaches the maximum stepping amount, the targeted current value reaches the maximum targeted current value. Therefore, as long as the control method of the motor 150 is the torque control method, a motor current value is maintained, as shown in FIG. 3, that is appropriate to the amount at which the foot switch 600 is stepped on. After the motor current value then reaches the maximum targeted current value, the motor current value is maintained at the maximum targeted current value. Since the maximum targeted current value is also smaller than the torque limit value, the torque limit function does not act during the time that the motor current value is maintained at the maximum targeted current value. To maintain a motor current value at this point that is appropriate to the amount at which the foot switch 600 is being stepped on, the motor current cannot be increased, even if the load from the body increases. Consequently, under the condition of an increasing load from the body, the rotation speed of the motor 150 decreases according to the stepping on the foot switch 600 when using the torque control method.

As shown in FIG. 4B, when the amount of stepping is at or below a predetermined value, the control method of the motor 150 switches from torque control method to speed control method. The switching shall be described further below in detail.

In step S8, the controller 202 displays the motor current value detected by the motor current detector 201 (torque value) on the external display unit 500.

In step S9, the controller 202 determines whether or not the amount at which the foot switch 600 is stepped on is at or below a predetermined value. This amount of stepping is smaller than, for example, the amount of stepping that is appropriate to the maximum targeted rotation speed when using the speed control method. If it is determined in step S9 that the amount at which the foot switch 600 is stepped on is at or below the predetermined value, the process returns to step S2. In that case, the control method of the motor 150 goes back from torque control method to speed control method. Since the targeted rotation speed has been decreased, the likelihood that the motor current value reaches or exceeds the torque limit value is presumed to be low, even if the motor 150 is controlled by the speed control method. It is therefore possible to switch the control method of the motor 150 to the speed control method. By doing so, the inserting or removing operations of the endoscope 100 are performed in an efficient way. If it is determined in step S9 that the amount at which the foot switch 600 is stepped on is not at or below the predetermined value, the process continues to step S10.

In step S10, the controller 202 determines whether or not the rotation speed of the motor 150 reaches or exceeds a predetermined switching rotation speed. The switching rotation speed is either equal to or larger than the maximum targeted rotation speed when using the speed control method, meaning equal to or larger than the targeted rotation speed at the time when the amount at which the foot switch 600 is stepped on is maximum. When it is determined in step S10 that the rotation speed of the motor 150 is at or above the predetermined switching rotation speed, the process returns to step S2. In that case, the control method of the motor 150 goes back from torque control method to speed control method. Since the motor current is controlled to be held constant when using the torque control method, the load from the body decreases and, as a consequence thereof, the rotation speed of the motor 150 rises. If the load from the body is little, it means that the torque of the motor 150 can also be decreased. Thus, the likelihood that the motor current value reaches or exceeds the torque limit value is presumed to be low, even if the motor 150 is controlled using the speed control method. Thus, by switching the control method of the motor 150 to speed control method, the inserting or removing operations of the endoscope 100 are performed in an efficient way. If it is determined in step S10 that the rotation speed of the motor 150 is not at or above the predetermined switching rotation speed, the process continues to step S11.

In step S11, the controller 202 determines whether or not the motor current value detected by the motor current detector 201 is at or above a torque limit value. The torque limit value is stored, for example, to the storage unit 204. If it is determined in step S11 that the motor current value is not at or above the torque limit value, the process returns to step S7. In that case, the torque control method for controlling the motor 150 is continued. If it is determined in step S11 that the motor current value is at or above the torque limit value, the process continues to step S12.

In step S12, the controller 202 stops the motor 150 by stopping the supply of motor current from the motor drive circuit 203. As mentioned above, when using the torque control method, the motor current value generally does not reach or exceed the torque limit value. However, there is the likelihood that, due to any sort of disturbance, the motor current value reaches or exceeds the torque limit value, even when using the torque control method, in which case the motor 150 is stopped.

In step S13, the controller 202 notifies the user that the torque limit function has been actuated. The notification is made using, for example, the external display unit 500.

In step S14, the controller 202 determines whether or not the stepping on the foot switch 600 is released. The stepping is with respect to both the F pedal 602 and the B pedal 604. If it is determined in step S14 that the stepping on the foot switch 600 is not been released, the process returns to step S13. If it is determined in step S14 that the stepping on the foot switch 600 is released, the process returns to step S2.

As described above, when the motor current is at or above the switching value that is less than the torque limit value, the control method of the motor 150 switches from speed control method to torque control method. Although the rotation speed of the insertion section 110 decreases when using the torque control method, the motor current is prevented from rising. In this way, the torque limit function is not frequently operated.

After switching to torque control method, when the amount at which the foot switch 600 is stepped on decreases or the rotation speed rises due to the decrease in the load from the body, the control method of the motor 150 switches from torque control method to speed control method. In this way, the user can perform the inserting or removing operations of the insertion section 110 in an efficient way.

Hereinbefore, the present invention stands explained based on the embodiment above, but the present invention shall clearly not be limited to the embodiment, and various modifications or applications may be made without departing from the spirit or scope of the general inventive concept of the present invention. The rotation body causing the insertion section 110 of the endoscope 100 to retreat has, in the aforementioned embodiment, for example, been the power spiral tube 132. However, the art underlying the embodiment is applicable to various kinds of insertion devices that cause the insertion section 110 to retreat by way of the rotation body.

Words such as "first" and "next" may have been used hereinbefore for convenience to describe the operations shown in the operation flowchart, but this does not mean that the operations necessarily have to be executed in that specific order.

It is further possible to store each of the processes according to the aforementioned embodiment as a program executable by the controller 202 being a computer. Other than that, they may be stored to the storage medium in an external storage device such as a magnetic disc, a light disc, or a semiconductor memory, for later distribution. The controller 202 may further read a program stored to the storage medium of an external storage device, and execute the above-identified processes by controlling the operations using the read program.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A control apparatus for an insertion device comprising an elongated insertion section, a rotate-driven self-propelling mechanism causing the insertion section to retreat, and a motor configured to transmit a driving force to the self-propelling mechanism, the control apparatus comprising:
    a controller comprising hardware, the controller being configured to:
        receive a detected drive current value driving the motor;
        when the drive current value is below a predetermined switching value, control the motor in a speed control method which controls the drive current value so that a rotation speed of the motor reaches a targeted rotation speed; and
        when the drive current value is at or above the switching value, control the motor by switching to a torque control method which controls a motor voltage of the motor so that a torque of the motor falls below a torque limit value by maintaining the drive current value at a maximum targeted value, which is above the switching value and below the torque limit value.

2. The control apparatus according to claim 1, wherein the controller is configured to control the motor so that the motor stops when the drive current value reaches the torque limit value.

3. The control apparatus according to claim 1, further comprising an operating unit for designating the targeted rotation speed,
    wherein the controller, after switching to the torque control method, is configured to control the motor by switching to the speed control method when an operation amount of the operating unit reaches or falls below a first predetermined value, or when the rotation speed of the motor reaches a second predetermined value.

4. An insertion device comprising:
    an elongated insertion section;
    a rotate-driven self-propelling mechanism causing the insertion section to retreat;
    a motor configured to transmit a driving force to the self-propelling mechanism; and
    a controller comprising hardware, the controller being configured to:
        receive a detected drive current value driving the motor;
        until the drive current value is at or above a predetermined switching value, control the motor in a speed control method which controls the drive current value so that a rotation speed of the motor reaches a targeted rotation speed; and
        when the drive current value is at or above the switching value, control the motor by switching to a torque control method which controls a motor voltage of the motor so that a torque of the motor falls below a torque limit value by maintaining the drive current value at a maximum targeted value, which is above the switching value and below the torque limit value.

5. A control method for controlling a self-propelling mechanism causing an insertion section to retreat, the method comprising:
    transmitting a driving force to the self-propelling mechanism with a rotary drive by a motor to cause the insertion section to retreat;
    detecting a drive current value driving the motor by a control apparatus configured to control the self-propelling mechanism;
    when the drive current value is below a predetermined switching value, controlling by the control apparatus the motor in a speed control method so that a rotation speed of the motor reaches a targeted rotation speed; and
    when the drive current value is at or above the switching value, controlling by the control apparatus the motor by switching to a torque control method, which controls a motor voltage of the motor so that a torque of the motor falls below a torque limit value by maintaining the drive current value at a maximum targeted value, which is above the switching value and below the torque limit value.

* * * * *